Figure 2:
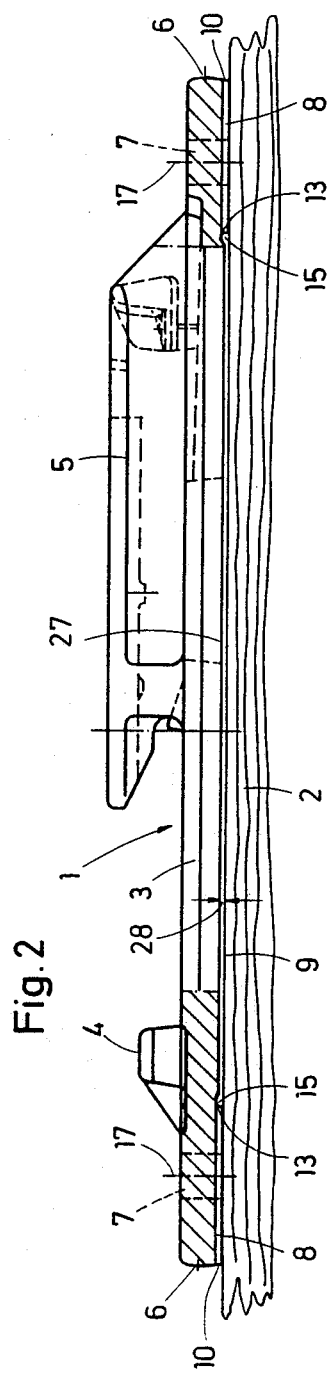

United States Patent [19]

Heim

[11] Patent Number: 4,921,168
[45] Date of Patent: May 1, 1990

[54] SUPPORT PLATE FOR MOUNTING RAILS OF RAILROAD TRACKS AND TRACK SWITCHES ON WOODEN SLEEPERS

[75] Inventor: Armin Heim, Kreuzlingen, Switzerland

[73] Assignee: Schwihag Gesellschaft für Eisenbahnoberbau mbH, Tägerwilen, Switzerland

[21] Appl. No.: 249,566
[22] PCT Filed: Dec. 15, 1987
[86] PCT No.: PCT/EP87/00781
§ 371 Date: Aug. 18, 1988
§ 102(e) Date: Aug. 18, 1988
[87] PCT Pub. No.: WO88/04707
PCT Pub. Date: Jun. 30, 1988

[30] Foreign Application Priority Data
Dec. 20, 1986 [DE] Fed. Rep. of Germany ....... 3643742

[51] Int. Cl.⁵ .................. E01B 9/40; E01B 9/68
[52] U.S. Cl. ...................... 238/287; 238/308
[58] Field of Search .............. 238/287, 297, 303, 308, 238/307, 298, 306, 286

[56] References Cited
U.S. PATENT DOCUMENTS
1,579,157 5/1926 Singeltary ........................ 238/298
1,583,774 5/1926 Boyce ............................. 238/298
1,834,256 12/1931 Ruping ............................ 238/303
2,713,975 7/1955 Martin ............................ 238/297

FOREIGN PATENT DOCUMENTS
2919461 11/1980 Fed. Rep. of Germany .
280001 11/1930 Italy ............................. 238/298
216352 8/1941 Switzerland .

Primary Examiner—Andres Kashnikow
Assistant Examiner—Mark T. Le
Attorney, Agent, or Firm—Toren, McGeady & Associates

[57] ABSTRACT

A support plate, particularly a ribbed plate for fastening rails of railroad tracks and track switches on wooden sleepers. The support plate is connected in the vicinity of its ends, in each instance, with the wooden sleeper by means of screws or the like which engage in the through-holes, whereas the rail flange is supported in each instance in the area of the plate between the fastening points on the sleeper side. On the underside of the plate, shoulders are provided or constructed only in the area of the through-holes for the fastening screws, which shoulders project out of the plane of the plate and have a thickness of approximately 1 mm to 2 mm. As a result of the cooperation between the shoulders and the fastening screws, the support plate has a convex curvature, so that its underside comes in supporting contact with the upper surface of the wooden sleeper.

19 Claims, 4 Drawing Sheets

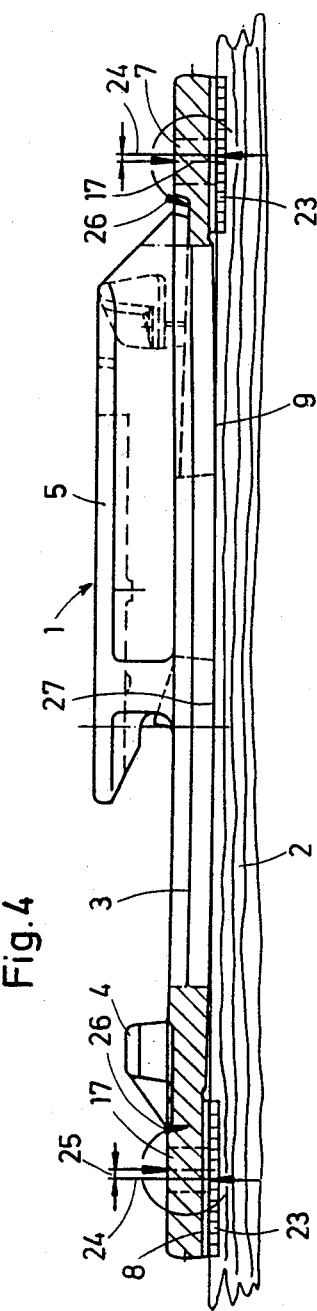
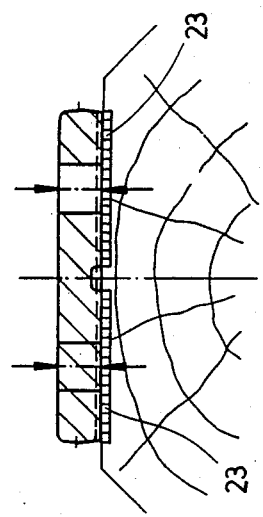
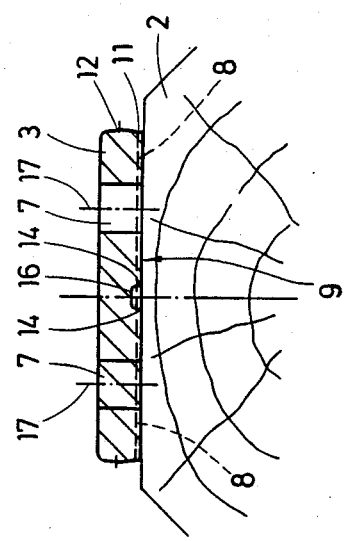

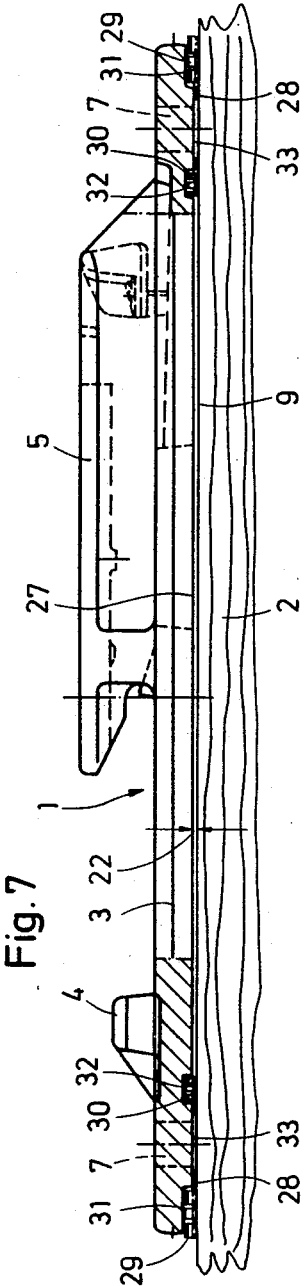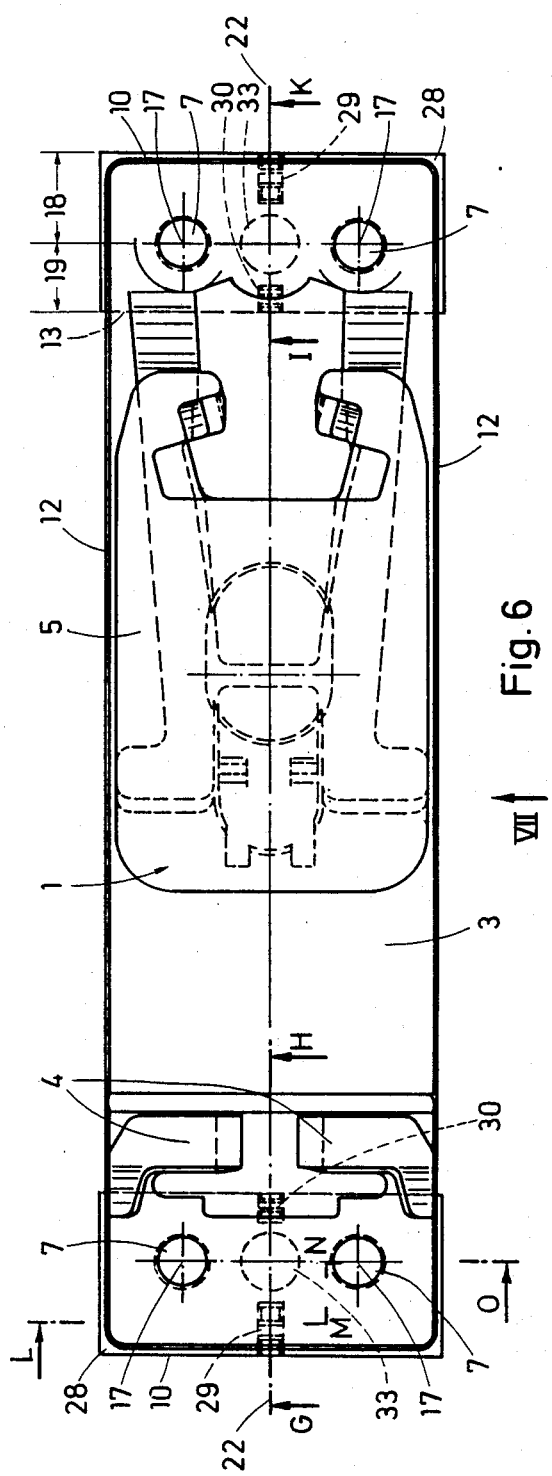

SUPPORT PLATE FOR MOUNTING RAILS OF RAILROAD TRACKS AND TRACK SWITCHES ON WOODEN SLEEPERS

The invention relates to a support plate, particularly a ribbed plate, for fastening rails of railroad tracks and track switches on wooden sleepers or another inhomogeneous material, which is connected in the vicinity of the ends in each instance with the sleeper by means of screws or the like which engage in the through-holes, whereas the rail flange is supported in the area of the plate between the fastening points on the sleeper side.

The support plates conventionally used during the construction of railroad tracks and track switches are fastened on the wooden sleepers by means of four screws or the like in each instance. In so doing, the aim is a fastening with the most constant possible screwing in forces. These screwing in forces should amount to up to 35 kN for a single screw, but can also reach up to 50 kN. The support plate can therefore be subjected to an area load of approximately 200 kN because of these high screwing in forces.

Since the fastening screws are applied relatively close to the ends of the support plate, a concave longitudinal deformation of the support plate occurs due to the high screwing in forces because these support plates usually only have a thickness which is limited to 16 or 10 mm and therefore only achieve a longitudinal stiffness which is much too low and is not sufficient for a force transmission without deformation.

In order for, e.g. a standard ribbed plate URP 206, as is currently used for fastening rails UIC 60 on wooden sleepers, to achieve a longitudinal stiffness which can enable an introduction of the maximum area load of 200 kN practically without deformation, it would have to obtain a thickness dimensioning of approximately 35 mm, instead of the standard thickness of 20 mm, if a sufficiently uniformly distributed surface pressure on the top of the wooden sleeper is to be achieved.

However, such an increased expenditure in material for the ribbed plates is prohibitive in practical use because of the resulting, considerably higher cost. Also, the reason for the concave curvature already occurring by means of the mounting of the plate has not been understood until now.

Therefore, it was previously taken into account that, in the conventional support plates, constant contact with the wooden sleeper exists only in the engagement area of the sleeper screw, whereas the middle area of each support plate is curved upward in a more or less concave manner, so that a hollow space is formed toward the top of the wooden sleeper where the rail flange has its support surface; the support plate alternately falls and rises—that is, it pumps, so to speak—over this hollow space when traveled over by the railroad car wheels, so that the upper surface of the wooden sleeper is damaged or even destroyed after a certain period of use. A loosening occurs because of the wear of the support plate, so that the track gauge can no longer be maintained, and the spring rings connected between the fastening screws and the support plate break. However, it also happens that the support plates themselves break in the critical area due to constant alternating stresses.

This shortcoming in known support plates causes relatively high maintenance costs because the wooden sleepers must often be removed because of damage to the top of the sleeper and readjusted after the removal of the support plate. However, it is then necessary simultaneously to dowel the holes provided until then for receiving the fastening screws and then to rebore them so that the fastening screws for the support plates can again be fastened in an optimal manner.

Since such recovery work on a wooden sleeper must be carried out approximately two to three times during its entire service life, considerable maintenance costs arise up to the point of its biological decay, that is, until it finally becomes unusable.

Since the spring rings break as a result of the pumping process, a replacement installation of new spring rings is required every 3 to 4 years, which also involves high costs. An elastically pretensioned support plate, which is produced by means of rolling or pressing, is known from DE-OS 29 19 461, its basic form being initially curved in a convex manner in such a way that after being fastened on the top of the wooden sleeper it does not lift up from the latter and therefore does not pump when being traveled over by railroad car wheels. The otherwise necessary spring rings are also dispensed with by means of this constructional and functional form.

In this known support plate, the support surface has a contact with the wooden sleeper which is constantly accompanied by pretensioning. However, it can only be produced from a work material whose tensile yield point is at least 520 N/mm$^2$.

Therefore, only simple, uncomplicated constructional forms of support plates can be produced relatively economically from such a material, which is to be processed only by means of rolling, pressing and drop forging.

For support plates which are constructed in a complicated manner, such as, e.g. slide chair and trestle plates, which are required for the construction of track switches, production cannot be carried out by means of rolling, pressing and drop forging for technical reasons.

The complicated support plates such as, e.g. slide chair and trestle plates, are presently produced economically by means of casting, wherein spheroidal cast GGG 40.3 is generally used. There is no question of using cast steel; one the one hand it is too expensive, on the other hand it cannot be cast with a sufficient degree of measurement accuracy and therefore requires costly subsequent work.

The object of the invention is to eliminate the shortcomings peculiar to the known support plates of the generic type. It therefore has the object of indicating a support plate of the type specified in more detail in the introductory part of the specification, which, after being secured on the wooden sleepers by means of screws or the like—that is, after the so-called mounting of the plate—ensures through simple means a support on the top of the sleeper which is constantly more secure and has a larger surface area than previously and eliminates the so-called pumping when traveled over by the wheels of a railroad car.

This object is met, according to the invention, by means of shoulders which project out of the plane of the plate, are provided or constructed at the underside of the plate only in the area of the through-holes for the fastening screws.

When the fastening screws penetrating the through-holes are tightened, the support plate is first clamped against the top of the wooden sleeper only with the shoulders, wherein, in the course of the constantly increasing screwing in forces, there occurs at the support plate a stress which produces a convex curving of its rail support area, by means of which the latter is pressed on the top of the wooden sleeper and is accordingly stabilized relative to the so-called pumping.

According to a further feature, the invention provides that the shoulders are formed on at the underside of the plate so as to form one piece.

However, according to another feature, the possibility is also taken into account that the shoulders are formed by means of shims of sheet metal or plastic and clamped or locked at the plate.

As a rule, it is sufficient that the shoulders have a thickness of approximately 1 to 1.5 mm. The free space for the sinking in of the shoulders, which free space is first produced relative to the top of the wooden sleeper by means of this thickness, is completely sufficient for ensuring the convex curvature clamping of the support plates after the tightening of the fastening screws.

The suggested solution, according to the invention, has the particular advantage that the support plates can be produced from any suitable work material and in the conventional manner, regardless of whether it has a simple or a complicated constructional form.

Support plates in which every through-hole is assigned its own shoulder area, according to the invention, and in which the adjacent shoulder areas are separated from one another by means of a longitudinal groove, have proven advisable. The distance of the defining border of the shoulders from the defining border of the respective through-hole can preferably be selected so as to be greater than the diameter of the through-hole.

However, in order to establish a convexly acting moment on the support plate during the mounting of the plate, it is important that the distance of the defining border of the through-hole from the adjacent end of the plate and from the respective outer transverse edge of the shoulder be dimensioned so as to be greater than the distance of the defining border of the through-hole from the inner transverse edge of the shoulder in question. The moments occurring during the tightening of the fastening screws then benefit the convex curvature of the rail support area of the support plate and, accordingly, the optimal pressing on of same on the top of the wooden sleeper. The respective rail is accordingly supported so as to be stable—in contrast to the previous known solutions.

According to a construction which has proven particularly advantageous the spacing of the outer and inner transverse edges of the shoulders relative to the defining border of the through-hole has a ratio of approximately 1.2:1, so that the distance of the outer transverse edges of the shoulder from the axis of the through-hole turns out to be approximately 20% greater than the distance of the inner transverse edge of the shoulder from the axis of the through-hole.

An optimal deformation behavior of the support plates is achieved, according to the invention, when the shoulders have a polygonal, e.g. approximately rectangular or square, outer contour, since the deformation behavior of the support plates is accordingly likewise influenced in an advantageous manner.

In addition, it is suggested according to the invention, that grooves be provided in the underside of the plate which adjoin the inner longitudinal edges and transverse edges of the shoulders, respectively. It also appears advantageous to provide corresponding annular grooves in the area of the two bore holes, the outwardly curved portions of the shoulder plates engaging in these annular grooves.

According to another construction suggestion of the invention, it is suggested, that the shim parts forming the shoulders comprise clamping or locking tongues which are pawled out of their plane and raised in a hook-like manner and which can be made to engage so as to align and hold in recesses provided in the underside of the plate. The shim parts forming the shoulders can extend along the entire width of the plates, wherein the clamping or locking tongues and a cut out portion, which is additionally provided between the latter, can be located approximately midway along the length of the shim parts.

So as not to produce any additional bending moment in cross section, a cut out portion or groove, respectively, can be provided on the longitudinal median line of the plate in the area of the shoulders in such a way that the resultants from the sleeper screw force lie in a plane with the resultants from the surface pressure. Previously, the plates were additionally curved transversely in a concave manner in the middle.

The subject matter of the invention is shown in the drawing by way of embodiment examples.

Figure 1:
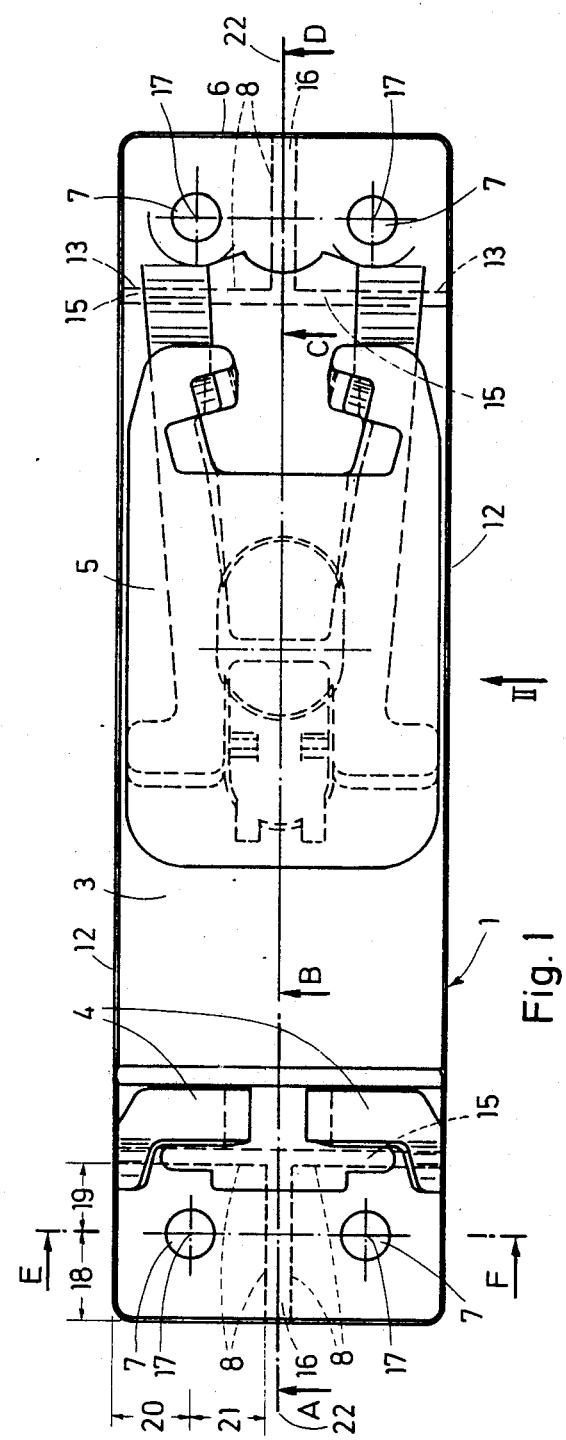

FIG. 1 shows the top view of a support plate which is constructed as a cast ribbed slide chair plate and comprises cast on shoulders, FIG. 2 shows the ribbed slide chair plate, according to FIG. 1, as seen in arrow direction II, and partly in longitudinal section along lines A-B and C-D in FIG. 1, FIG. 3 shows a section along line E-F in FIG. 1, FIG. 4 shows a view of the ribbed slide chair plate corresponding to FIG. 2, wherein the forces and moments occurring during the tightening of the fastening screws are shown, and also the resultant produced from the exactly defined surface pressure occurring during the tightening of the fastening screws is indicated, FIG. 5 shows a view corresponding to FIG. 3, wherein the forces occurring by means of the tightening of the fastening screws and the resultant from the surface pressures are indicated, FIG. 6 shows a top view of a modified constructional type for a ribbed slide chair plate, which top view corresponds to FIG. 1, FIG. 7 shows a view of the ribbed slide chair plate in arrow direction 7 of FIG. 6, wherein it is shown in partial section respectively in the regions G-H and I-K of the figure, and in which the shoulders comprise sheet metal plates or plastic parts which are placed underneath.

Figure 9:
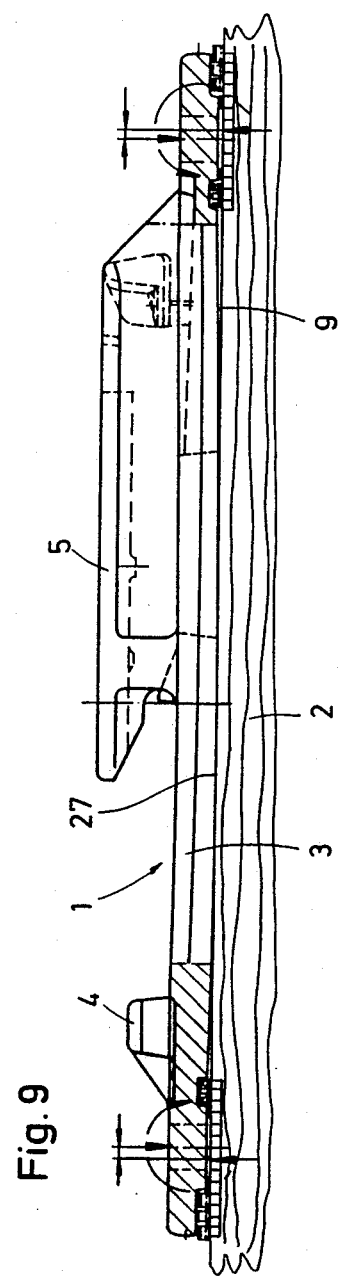
Figure 10:
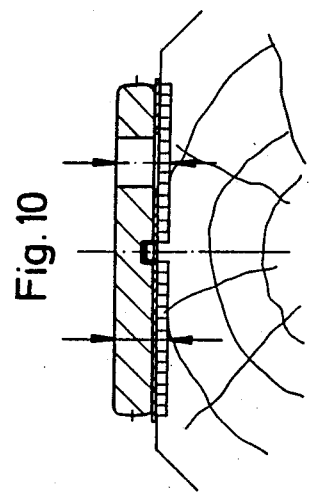
Figure 8:
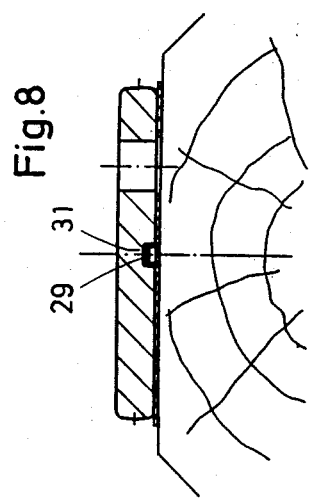

FIG. 8 shows a section along line L-M-N-O in FIG. 6,

FIG. 9 shows a view corresponding to FIG. 7, wherein, however, the forces and moments occurring during the tightening of the fastening screws and the resultant from the surface pressure are indicated and FIG. 10 shows a section corresponding to FIG. 8 with an indication of the forces occurring during the tightening of the fastening screws and the resultants from the surface pressures, both of which lie in a plane and accordingly prevent a moment leading to a bending in the transverse direction.

In FIGS. 1 to 5 of the drawing, a cast ribbed slide chair plate 1, as is used in connection with wooden sleepers 2 for the construction of railroad switches, is shown as an example of application of the invention.

The ribbed slide chair plate 1 comprises a relatively long and narrow support plate 3 which carries the ribs 4 on the one hand and the slide chair 5 on the other hand so as to be fixed in one piece on its upper side.

The support plate 3 is provided with two through-holes 7 respectively at its two ends, that is, in the vicinity of its transverse edges 6, which through-holes 7 serve to receive the fastening screws—not shown—for forming the fastening points on the sleeper side.

In the area between the through-holes 7 for the fastening screws, the support plate 3 itself forms the support for the rail flange of a fixed rail—not shown—on the one hand, whereas, on the other hand, the slide chair 5 serves as a support for the rail flange of a switch tongue—also not shown.

At the underside, the support plate 3 is equipped, only in the area of the through-holes 7 for the fastening screws, with shoulders 8 projecting from the plane of the plate, which shoulders 8 have a relatively small height, e.g. between 1.0 and 2.0 mm, and come in supporting contact with the upper surface 9 of the sleeper.

In the ribbed slide chair plate 1, according to FIGS. 1 to 5, the shoulders 8 are formed on at the underside of the support plate 3 in a fixed manner so as to form one piece, specifically in such a way that every through-hole area 7 is assigned its own shoulder area 8. These shoulders 8 have a polygonal, e.g. an approximately square, outer contour. The outer transverse edge 10 of the shoulders 8 is situated so as to cover the outer transverse edge 6 of the support plate 3, whereas their outer longitudinal edge approximately coincides with the longitudinal edge 12 of the support plate 3.

The inner transverse edge 13 of each shoulder 8 is defined by a transverse groove 15 located in the underside of the support plate 3, whereas the inner longitudinal edges 14 of same adjoin a longitudinal groove 16 in each instance, which longitudinal groove 16 is located in the underside of the support plate 3 and lies on the longitudinal median line 22—22 of the support plate 3.

Every shoulder 8 has a relative position relative to the respective through-hole area 7 of the support plate 3 such that its outer transverse edge 10 is at a distance 18 from the axis 17 of this through-hole 7, which distance 18 is greater than the distance 19 of the inner transverse edge 13 from this axis 17.

The distance 20 of the outer longitudinal edge 11 of each shoulder 8 from the axis 17 of the respective through-hole 7 should advisably have the same dimensioning as the distance 21 of the inner longitudinal edge 14 from this axis 17.

In practical use, it has proven advantageous if the ratio of the distances 18 and 19 of the outer and inner transverse edges 10 and 13 of the shoulder relative to the longitudinal axis 17 of the through-hole 7 is approximately 1.2:1, so that the distance of the defining border of the through-hole from the outer transverse edge 10 turns out to be 20% greater than the distance of the inner defining edge 13 from this defining border of the through-hole.

When attaching the ribbed slide chair plate 1 at the wooden sleeper 2, the support plate 3 first rests only with the lower end faces of its shoulders 8 on the upper surface 9 of the wooden sleeper 2, as is made clear by FIG. 2. However, the area of the support plate 3 carrying the ribs 4 and the slide chair 5 is located at a distance 28 from the upper surface 9 of the sleeper, as is likewise shown in FIG. 2.

As soon as the fastening screws—not shown—are screwed into the wooden sleeper 2 in the area of the through-holes 7 and are tightened until reaching the maximum possible screwing in force of 50 kN per fastening screw, a corresponding surface pressure occurs between the lower end face of the shoulders 8 and the upper surface 9 of the wooden sleeper 2, which is shown in FIGS. 4 and 5 of the drawing by means of the surface pressure fields 23 provided in each instance with vertical hatching.

Since the resultant from the surface pressure 24 of each shoulder area 8 has an offset position 25 in each instance relative to the axis 17 of the respective through-hole 7, which offset position 25 is determined by the difference between the two distances 18 and 19, a torque occurs by means of the tightening of the fastening screws in the area of each shoulder area 8, which torque acts on the support plate 3 in the direction of the arrow 26 and accordingly bends or deforms the latter downward in a convex manner until it contacts the top of the wooden sleeper, as can be seen in FIG. 4. Accordingly, the distance 22 between the underside 27 of the support plate 3 and the upper surface 9 of the sleeper is overcome, i.e. the underside 27 of the support plate 3 contacts the upper surface 9 of the sleeper so as to be supported, as can be seen in FIG. 4.

The bending moment which is brought about by means of the fastening screws and which causes the convex deformation of the support plate 3 is thus dependent on the offset position 25 between the resultants of the surface pressure 24 of the shoulders and the sleeper screw axis 17 of the respective through-hole 7 for this fastening screw. The convex twisting of the support plate 3 brought about by means of this bending moment is due to the fact that the shoulders 8 can sink into the upper surface 9 of the wooden sleeper 2 in the area of their inner transverse edge 18 somewhat more deeply than their outer transverse edges. Because of the convex curvature and deformation, respectively, of the support plate 3 and the supporting contact of its underside 27 on the upper surface 9 of the wooden sleeper 2 resulting from this, no alternating stresses occur in the critical area of the ribbed slide chair plate when traveled over by a rail-guided vehicle; rather, only a dynamic load occurs. The so-called pumping process of the ribbed slide chair plate 1 relative to the wooden sleeper 2 is accordingly completely eliminated. The upper surface 9 of the wooden sleeper is spared, so that the service life of the latter is increased by a multiple of the previous service life relative to mechanical destruction. The constant monitoring against loosening and breakage of the ribbed slide chair plates 1 is dispensed with and the maintenance work resulting from it can be avoided. Moreover, the spring rings, which were previously provided in a conventional manner between the fastening screws and the ribbed slide chair plate, are dispensed with, so that it is no longer necessary to monitor them and exchange them during the biological service life of a wooden sleeper 2.

The ribbed slide chair plate 1 shown in FIGS. 6 to 10 works basically in the same manner as that according to FIGS. 1 to 5. The only difference is that the shoulders 8 at the underside 27 of the support plate 3 are not cast on in a single piece, rather they are formed by means of one-piece shim parts 28 consisting of sheet metal or plastic, which can be clamped or locked at the support plate 3. Also, the shim parts 28 serving as shoulders have a thickness which is between 1 mm and 2 mm and, moreover, they are constructed in such a way that their outer transverse edge 10 has a distance 18 from the longitudinal axis of the through-holes 7 which is greater than the distance 19 of their inner transverse edge 13 from the axis 17 of the through-holes 7.

As distinguished from the shoulders 8 in the embodiment example according to FIGS. 1 to 5, the shim parts in the embodiment example according to FIGS. 6 to 10 are constructed in such a way that they continue uninterruptedly along the entire width of the support plate.

The shim parts 28 are provided with clamping and locking tongues 29 approximately midway along the length, which clamping and locking tongues 29 are pawled out of their plane and raised in a hook-like manner and achieve an aligning and holding engagement with recesses provided in the underside 27 of the plate.

Moreover, in the area between the clamping and locking tongues 29 and 30, each of the shim parts 28 comprises an additional cut out portion 33, e.g. in the shape of a round hole, which can be constructed so as to be somewhat greater than the through-holes 7 in the support plate 3. For the use of shim parts 28 as shoulders, ribbed slide chair plates 1 constructed in a conventional manner are suitable in a practically unaltered form. It may only be necessary to work recesses 31 and 32 into the underside 27, which recesses 31 and 32 can receive the clamping and locking tongues 29 and 30 of the shim parts 28. Of course, it would also be conceivable to use shim parts 28 without clamping and locking tongues 29 and 30 in combination with the conventional ribbed slide chair plates 1 and to effect their holding connection with the support plate 3 by means of a contact adhesive or the like.

Of course, the outfitting with shoulders 8 and shim parts 28 is not limited to the ribbed slide chair plates shown in the drawing as embodiment examples. On the contrary, it can be used with ribbed plates of every constructional type, e.g. with the conventional K-ribbed plates, trestle plates or the like.

I claim:

1. Support plate, particularly a ribbed plate, for fastening rails of railroad tracks and track switches on wooden sleepers, each rail having a flange, the support plate being connected in the vicinity of the ends thereof with the sleeper by means of screws which engage in through-holes defined in the support plate, whereas the rail flange is supported in the area of the plate between the through-holes forming the fastening points to the sleeper, wherein the improvement comprises that shoulders (8 and 28, respectively) are provided at the underside (27) of the plate only in the area of the through-holes (7) for the fastening screws, which shoulders (8 and 28, respectively) project out of the plane of the plate, and that, in the area between the shoulders, the support plate is configured such that tightening of the screws results in a convex elastic curving of the support plate, so that any distance between the underside (27) of the plate and the top surface (9) of the sleeper is eliminated.

2. Support plate according to claim 1, wherein the shoulders (8) are formed on at the underside (27) of the plate in one piece.

3. Support plate according to claim 1, wherein the shoulders are formed by means of shim parts (28) of sheet metal and are fixed at the underside (27) of the plate.

4. Support plate according to one of claims 1 to 3, wherein the shoulders (8 and 28, respectively) have a thickness of approximately 1 to 2 mm.

5. Support plate according to claim 1, wherein every through-hole (7) is assigned its own shoulder area having a border (8), the shoulder areas being separated from one another by means of a groove (16) and wherein the distance between the border of each shoulder (8) and the through-hole (7) is greater than the diameter of the through-hole (7).

6. Support plate according to claim 1, wherein each shoulder has an outer transverse edge and an inner transverse edge, and the distance (18) between the longitudinal axis (17) of the through-hole (7) and the outer transverse edge (10) of the shoulder is greater than the distance (19) between the axis (17) of the through-hole (7), and the inner transverse edge (13) of the shoulder (8 and 28, respectively).

7. Support plate according to claim 6, wherein the ratio of the distance between the outer transverse edge (10) of the shoulder and the axis of the through-hole and the distance between the inner transverse edge (13) of the shoulder and the axis (17) of the through-hole (7) is approximately 1.2 to 1.

8. Support plate according to claim 1, wherein the shoulders (8 and 28, respectively) have a polygonal outer contour.

9. Support plate according to claim 7, wherein each shoulder has an inner longitudinal edge, and wherein grooves (15 and 16) are provided in each instance in the underside (27) of the plate, which grooves adjoin the inner longitudinal edge (13) of the shoulder and the inner transverse edge (14) of the shoulder.

10. Support plate according to claim 3, wherein the shim parts (28) forming the shoulders comprise clamping and locking tongues (29, 30) which are pawled out of their plane and are raised in a hook-like manner and which can be brought into an aligning and holding engagement with recesses (31, 32) provided in the underside (27) of the plate.

11. Support plate according to claim 10, wherein the shim parts (28) forming the shoulders extend along the entire width of the plate, wherein wherein the clamping and locking tongues (29, 30), as well as a cut out portion (33) additionally provided between the latter, are located approximately midway along the length of the shim parts (28).

12. Support plate according to claim 9, wherein the groove (16) adjoining the longitudinal edge (22-22) is constructed such that no moment occurs from the transverse distance of the bore holes, and the resultants of the sleeper screw axes are located in the same plane as the two resultants from the two area loads of the shoulders.

13. Support plate according to claim 1, wherein the shoulders are formed by means of shim parts (28) and are fixed at the underside (27) of the plate.

14. The support plate according to claim 13, wherein the shim parts are fixed to the underside of the plate by clamping.

15. The support plate according to claim 13, wherein the shim parts are fixed to the underside of the plate by cementing.

16. The support plate according to claim 13, wherein the shim parts are fixed to the underside of the plate by locking.

17. The support plate according to claim 4, wherein the thickness of the shoulders is 1.5 mm.

18. The support plate according to claim 8, wherein the outer contour of the shoulders is rectangular.

19. The support plate according to claim 8, wherein the outer contour of the shoulders is square.

* * * * *